(12) United States Patent
Phamduy et al.

(10) Patent No.: US 10,395,099 B2
(45) Date of Patent: Aug. 27, 2019

(54) SYSTEMS, DEVICES, AND METHODS FOR THREE-DIMENSIONAL ANALYSIS OF EYEBAGS

(71) Applicant: L'Oreal, Paris (FR)

(72) Inventors: Theresa Phamduy, Jersey City, NJ (US); Kelsey Norwood, Scotch Plains, NJ (US)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 15/269,246

(22) Filed: Sep. 19, 2016

(65) Prior Publication Data

US 2018/0082108 A1 Mar. 22, 2018

(51) Int. Cl.
*G06K 9/46* (2006.01)
*G06K 9/62* (2006.01)
(Continued)

(52) U.S. Cl.
CPC ........ *G06K 9/00288* (2013.01); *A61B 5/0077* (2013.01); *A61B 5/442* (2013.01);
(Continued)

(58) Field of Classification Search
CPC ........... G06K 9/00214; G06K 9/00221; G06K 9/00228; G06K 9/00234; G06K 9/00241;
(Continued)

(56) References Cited

U.S. PATENT DOCUMENTS

| 6,571,003 | B1 * | 5/2003 | Hillebrand | ........... | A61B 5/0064 |
| | | | | | 382/100 |
| 2002/0015527 | A1 * | 2/2002 | Nambu | .............. | G06K 9/00221 |
| | | | | | 382/218 |

(Continued)

FOREIGN PATENT DOCUMENTS

| JP | 2015-082130 A | 4/2015 |
| WO | 2012/126135 A1 | 9/2012 |
| WO | 2015/017687 A2 | 2/2015 |

OTHER PUBLICATIONS

Fukuda, Y., et al., "A New Method to Evaluate Lower Eyelid Sag Using Three-Dimensional Image Analysis," International Journal of Cosmetic Science 27(5):283-290, Oct. 2005.

(Continued)

*Primary Examiner* — Dwayne D Bost
*Assistant Examiner* — Stephen M Brinich
(74) *Attorney, Agent, or Firm* — Christensen O'Connor Johnson Kindness PLLC

(57) ABSTRACT

In some embodiments of the present disclosure, a system for processing three-dimensional face scan data is provided. A three-dimensional scanner produces an image of a face including an area of interest that includes an eyebag area. A profile of the eyebag area is determined by the system. In some embodiments, the profile is determined based on a vertical slice at the center of the eyebag area. Profiles for multiple sets of scan data may be compared to determine quantitative differences between eyebag profiles. These differences may be used for quantitatively comparing the effects of products applied to the eyebag area between scans. These differences may also be used for predictively generating three-dimensional models to illustrate predicted effects of the use of a product on a face.

16 Claims, 10 Drawing Sheets

(51) Int. Cl.
*A61B 5/00* (2006.01)
*G06K 9/00* (2006.01)

(52) U.S. Cl.
CPC ..... *G06K 9/00214* (2013.01); *G06K 9/00248* (2013.01); *G06K 9/4642* (2013.01); *G06K 9/6206* (2013.01); *G06K 9/6215* (2013.01); *G06K 2209/40* (2013.01)

(58) Field of Classification Search
CPC ........... G06K 9/00248; G06K 9/00255; G06K 9/00261; G06K 9/00288; G06K 9/00295; G06K 9/00302; G06K 9/00308; G06K 9/00315; G06K 2009/00322; G06K 2009/00328; G06K 9/00201; G06K 9/00208; G06K 9/4642; G06K 9/6206; G06K 9/6215; G06K 9/6217
USPC ................ 382/115–118, 128, 181, 170, 154; 348/47–48
See application file for complete search history.

(56) References Cited

U.S. PATENT DOCUMENTS

| | | | | |
|---|---|---|---|---|
| 2006/0126905 | A1* | 6/2006 | Loo | G06K 9/00255 382/118 |
| 2006/0206724 | A1* | 9/2006 | Schaufele | G06F 21/32 713/186 |
| 2007/0122007 | A1* | 5/2007 | Austin | G06K 9/00221 382/118 |
| 2008/0136814 | A1 | 6/2008 | Chu et al. | |
| 2009/0185723 | A1* | 7/2009 | Kurtz | G06K 9/00288 382/118 |
| 2009/0309878 | A1* | 12/2009 | Otani | G06K 9/00208 345/427 |
| 2013/0142398 | A1* | 6/2013 | Polimeno | G06K 9/00221 382/110 |
| 2013/0286161 | A1* | 10/2013 | Lv | G06K 9/00214 348/46 |
| 2013/0329966 | A1* | 12/2013 | Hildreth | G06K 9/00335 382/115 |
| 2014/0266604 | A1* | 9/2014 | Masood | G06K 9/00221 340/5.83 |
| 2014/0355830 | A1* | 12/2014 | Park | G06K 9/00228 382/103 |
| 2015/0169938 | A1* | 6/2015 | Yao | G06K 9/00261 382/103 |
| 2015/0178554 | A1* | 6/2015 | Kanaujia | G06T 19/20 382/118 |
| 2016/0026342 | A1* | 1/2016 | Cohen | G06F 3/0482 715/821 |
| 2017/0169204 | A1* | 6/2017 | Fadell | G06F 21/32 |

OTHER PUBLICATIONS

International Search Report dated Dec. 14, 2017, issued in corresponding International Application No. PCT/US2017/050051, filed Sep. 5, 2017, 44 pages.
Written Opinion dated Dec. 14, 2017, issued in corresponding International Application No. PCT/US2017/050051, filed Sep. 5, 2017, 8 pages.

* cited by examiner

SYSTEMS, DEVICES, AND METHODS FOR THREE-DIMENSIONAL ANALYSIS OF EYEBAGS

SUMMARY

In some embodiments, a computer-implemented method of processing three-dimensional face scan data is provided. A facial analysis device receives first face scan data representing a three-dimensional scan of a face. The facial analysis device determines a first model of an eyebag area of the first face scan data. The facial analysis device determines a first score based on the first model, and stores the first score in a scan data store.

In some embodiments, a system for processing three-dimensional face scan data is provided. The system comprises a three-dimensional scanner and a facial analysis device communicatively coupled to the scanner. The facial analysis device is configured to perform actions including the following: receiving, from the three-dimensional scanner, first face scan data representing a three-dimensional scan of a face; determining a first model of an eyebag area of the first face scan data; determining a first score based on the first model; and storing the first score in a scan data store.

In some embodiments, a system for processing three-dimensional face scan data is provided. The system comprises circuitry for receiving first face scan data representing a three-dimensional scan of a face; circuitry for determining a first model of an eyebag area of the first face scan data; circuitry for determining a first score based on the first model; and circuitry for storing the first score in a scan data store.

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

In the cosmetic industry, the use of three-dimensional analysis tools provides new avenues for technical measurement of product efficacy and communication of product benefit to consumers. However, no in vivo measurement exists to describe or evaluate the eyebag area in a quantitative manner. What is desired are systems and methods that provide automated analysis of three-dimensional scans of the eyebag area and that are capable of generating an output to an end user (such as a consumer, a clinician, a scientist, or another type of user) usable for assessment.

The use of three-dimensional imaging technology is novel for quantitative measurement of eyebags, a physical facial feature that lacks geometric information in the literature. In addition to quantitative measurement, eyebag models may also be useful for determining mechanisms of product action on the eyebag area.

Three-dimensional measurement is achieved through a noncontact imaging technique, which provides accurate information about the in vivo eyebag shape and is advantageous compared to subjective visual grading by a trained clinician. Further, three-dimensional scanning devices provide very fine-grained data for analysis, and so can allow detailed comparison of multiple scans. This detailed comparison can then be used to track the shape of the eyebag area on a user's face over time, such as both before and after applying a product intended to change the shape and thereby reduce the appearance of the eyebags in order to quantitatively test product efficacy. In addition, individual measurements can also be used to grade the severity of the eyebag for diagnostic assessments. In some embodiments of the present disclosure, face surface structure is captured with a three-dimensional imaging device, which results in a stored three-dimensional scan that can be displayed on a display device to focus on the eyebag area. In some embodiments, for each three-dimensional scan, a midplane may be drawn between the highest z-point and the lowest z-point of the geometry. The spread of measured points above and below this plane may be calculated as a single metric, such as a standard deviation of a histogram. To users, the singular metric can be presented as a diagnostic of the current "flatness" state of the eyebag. Alternatively, subsequent metrics can be compared to characterize the amount of "flattening" the eyebag has undergone to track progress or product effect. In some embodiments, for each three-dimensional scan, a vertical cut is made in the middle of the eyebag. The analysis may use data acquisitions from different timepoints. Based on characterization of the scans (e.g., area under curve, eyebag height, tear trough valley depth, arc length, slope, etc.) of these curves, product effect can be assessed. For users, this may be presented as a tracking metric.

Figure 1:
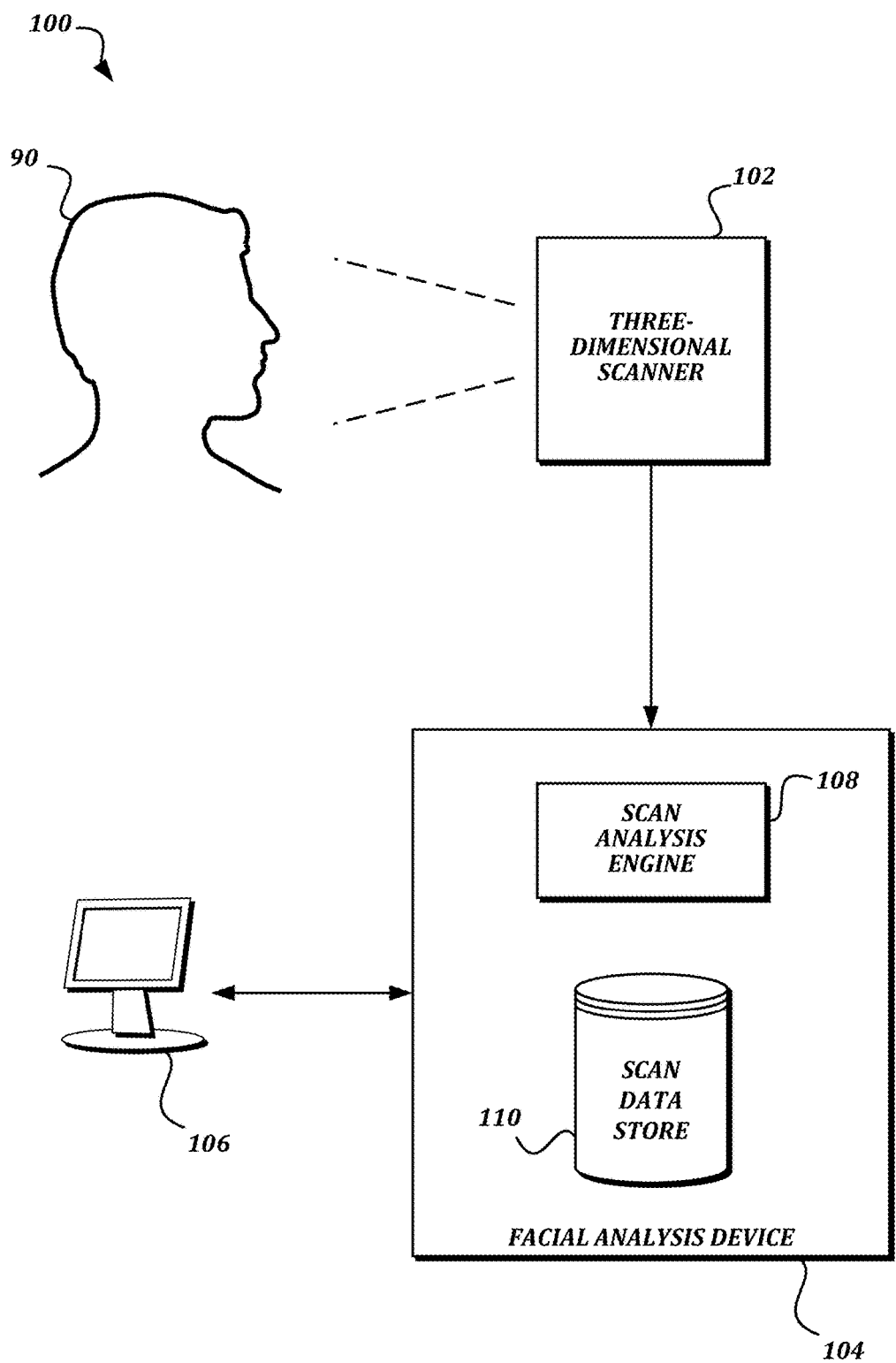
FIG. 1 is a schematic diagram that illustrates components of an exemplary embodiment of a system for analyzing eyebags according to various aspects of the present disclosure.

FIG. 1 is a schematic diagram that illustrates components of an exemplary embodiment of a system for analyzing eyebags according to various aspects of the present disclosure. As illustrated, the system 100 includes a three-dimensional scanner 102, a facial analysis device 104, and a display 16. The three-dimensional scanner 102 is any suitable device that can generate a three-dimensional representation of an object such as a face. The three-dimensional scanner 102 may use fringe-projection, stereophotogrammetry, or any other suitable technique for generating the three-dimensional representation. One example device that would be suitable for use as the three-dimensional scanner 102 is the DermaTOP produced by EOTECH SA. Another example device that would be suitable for use as the three-dimensional scanner 102 is the VECTRA M3 produced by Canfield Scientific, Inc. Another example device that would be suitable for use as the three-dimensional scanner 102 is an attachment device for a smartphone that is capable of generating three-dimensional models from camera images or other data sources. These examples should not be seen as limiting, as any other device with similar functionality may be used.

The facial analysis device 104 is a computing device that is communicatively coupled to the three-dimensional scanner 102. In some embodiments, some or all of the functionality of the facial analysis device 104 is provided by a computing device incorporated into the three-dimensional scanner 102. In some embodiments, some or all of the functionality of the facial analysis device 104 is provided by a separate computing device such as a desktop computing device, a laptop computing device, a tablet computing device, a smartphone, a device of a cloud service, and/or any other type of computing device.

The facial analysis device includes a scan analysis engine 108 and a scan data store 110. In some embodiments, the scan analysis engine 108 is configured to receive scan data from the three-dimensional scanner 102, to generate eyebag models based on the scan data, to compare eyebag models to determine differences, and to use the computed differences in various ways. In some embodiments, the scan data store is configured to store one or more of scan data, model data, and difference data. Further details of the configuration of the scan analysis engine 108 and the scan data store 110 are provided below.

In general, the term "engine" as used herein refers to logic embodied in hardware or software instructions, which can be written in a programming language, such as C, C++, COBOL, JAVA™, PHP, Perl, HTML, CSS, JavaScript, VBScript, ASPX, Microsoft .NET™ languages such as C#, application-specific languages such as Matlab, and/or the like. An engine may be compiled into executable programs or written in interpreted programming languages. Engines may be callable from other engines or from themselves. Generally, the engines described herein refer to logical modules that can be merged with other engines or applications, or can be divided into sub-engines. The engines can be stored in any type of computer readable medium or computer storage device and be stored on and executed by one or more general purpose computers, thus creating a special purpose computer configured to provide the engine. Accordingly, the devices and systems illustrated herein include one or more computing devices configured to provide the illustrated engines, though the computing devices themselves have not been illustrated in every case for the sake of clarity.

As understood by one of ordinary skill in the art, a "data store" as described herein may be provided by any suitable device configured to store data for access by a computing device. One example of a data store is a highly reliable, high-speed relational database management system (RDBMS) executing on one or more computing devices and accessible locally or over a high-speed network. However, any other suitable storage technique and/or device capable of quickly and reliably providing the stored data in response to queries may be used, such as a key-value store, an object database, and/or the like. The computing device providing the data store may be accessible locally instead of over a network, or may be provided as a cloud-based service. A data store may also include data stored in an organized manner on a computer-readable storage medium, as described further below. Another example of a data store is a file system or database management system that stores data in files (or records) on a computer readable medium such as flash memory, random access memory (RAM), hard disk drives, and/or the like. One of ordinary skill in the art will recognize that separate data stores described herein may be combined into a single data store, and/or a single data store described herein may be separated into multiple data stores, without departing from the scope of the present disclosure.

The display 106 is communicatively coupled to the facial analysis device 104. Any type of display device may be used as the display 106, such as an LCD monitor, a CRT monitor, a projector, a touchscreen device, a smartphone, and/or the like. In some embodiments, the display 106 is separate from the facial analysis device 104. In some embodiments, the display 106 is combined with the facial analysis device 104 and/or the three-dimensional scanner 102.

In some embodiments, the system 100 provides additional interfaces for managing user accounts and historical information. For example, the facial analysis device 104 may store user account information, and a user 90 may use a user name and password to access an account on the facial analysis device 104 that stores information about the user 90 such as past scan data, demographic information, purchase history, previously used products, and/or the like. In some embodiments, the scan data store 110 may be provided by a server or cloud service, and the facial analysis device 104 may encrypt and/or anonymize face scan data, demographic information, personally identifiable information, and/or any other information pertaining to the user 90 before transmission to the scan data store 110.

Figure 2A:
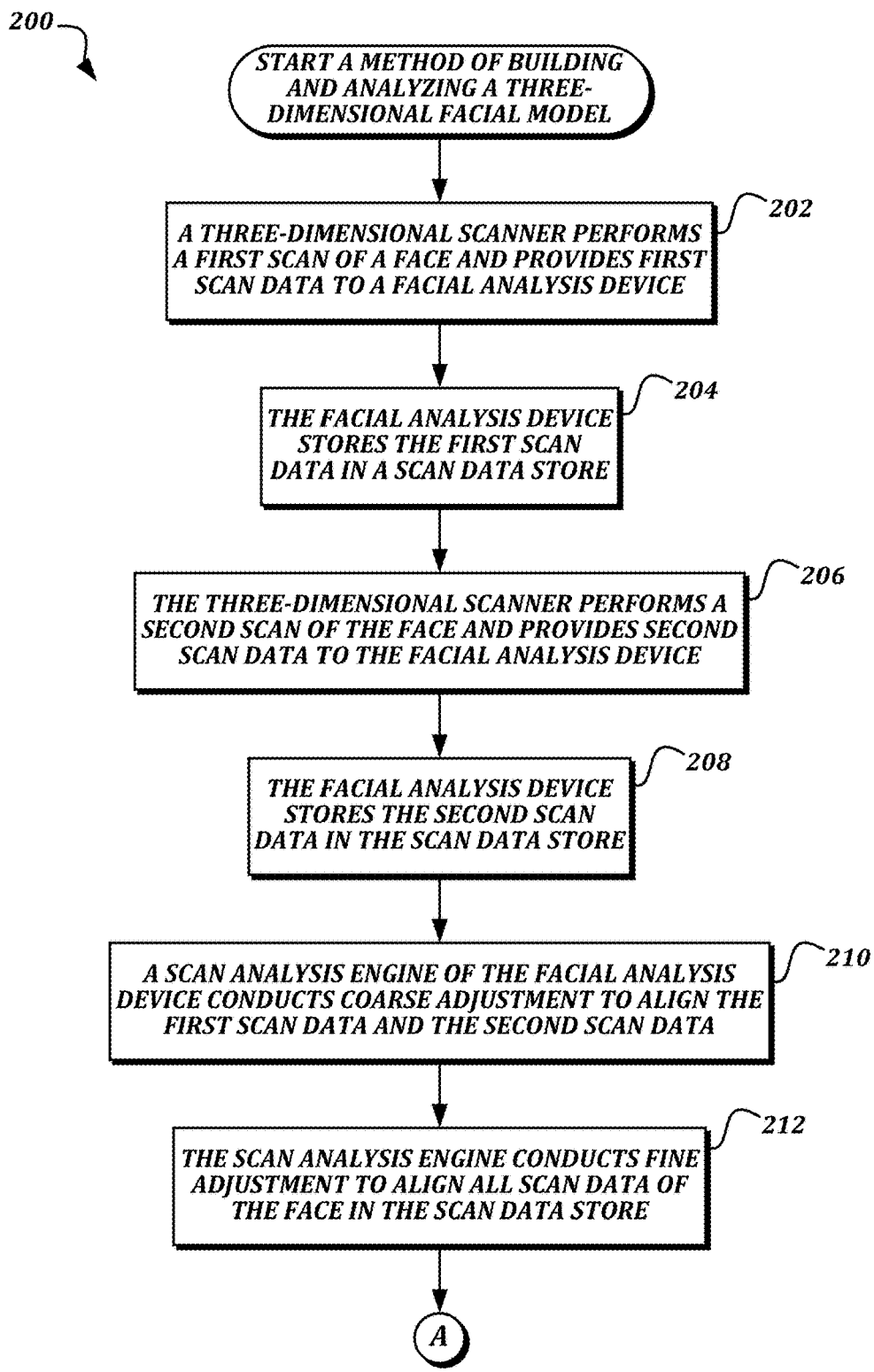
FIGS. 2A-2B are a flowchart that illustrates an exemplary embodiment of a method of building and analyzing a facial model according to various aspects of the present disclosure.
Figure 2B:
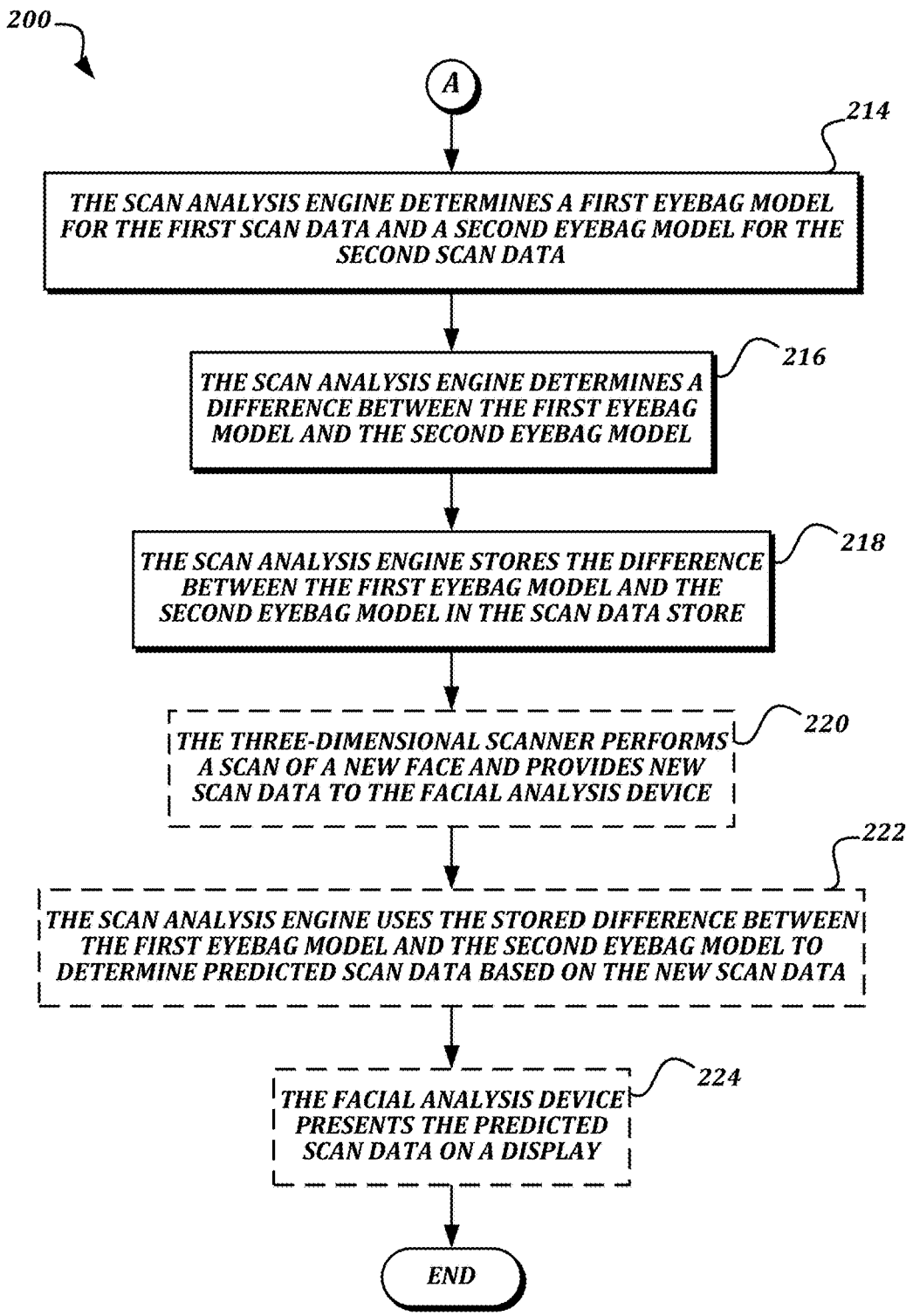

FIGS. 2A-2B are a flowchart that illustrates an exemplary embodiment of a method of building and analyzing a facial model according to various aspects of the present disclosure. From a start block, the method 200 proceeds to block 202, where a three-dimensional scanner 102 performs a first scan of a face and provides first scan data to a facial analysis device 104. The first scan data is a three-dimensional representation of the face as obtained by the three-dimensional scanner 102. In some embodiments, the first scan data may include a surface geometry saved in a .ply or .stl file, while in some embodiments, other suitable data formats may be used. Next, at block 204, the facial analysis device 104 stores the first scan data in a scan data store 110. In some embodiments, the entire scan data received from the three-dimensional scanner 102 is stored in the scan data store 110. In some embodiments, a region of interest from the scan data is stored in the scan data store 110 and a remainder of the scan data is discarded. In some embodiments, a model may be generated (as described below), and the model may be stored in the scan data store 110 instead of the entirety of the scan data. In some embodiments, a model score may be generated (as described below), and the model score may be stored in the scan data store 110 instead of the entirety of the scan data or the model.

At block 206, the three-dimensional scanner 102 performs a second scan of the face and provides second scan data to the facial analysis device 104, and at block 208, the facial analysis device 104 stores the second scan data in the scan data store 110. The actions performed at blocks 206 and 208 are similar to the actions performed at blocks 202 and 204, but are later in time. In some embodiments, the second scan may be performed after a period of time has elapsed, during which time a product may have been applied to the face 90. In this way, the second scan may be performed to determine the effect of the product on the face 90 by comparing it to the first scan. In some embodiments, such as embodiments wherein a single scan is conducted and no comparisons between models or model scores are performed, only the first scan is performed and only the first scan data is stored.

In some embodiments, images of the same face 90 taken at multiple timepoints may be subject to misalignment due to imperfect repositioning of the face 90 with respect to the three-dimensional scanner 102 during each scan. Accordingly, automated realignment of surface geometries of the scan data may be desirable. One non-limiting example of computerized alignment is described in blocks 210 and 212. At block 210, a scan analysis engine 108 of the facial analysis device 104 conducts coarse adjustment to align the first scan data and the second scan data. In some embodiments, pair-wise coarse adjustment may be performed. In such embodiments, the first scan data is aligned to the second "anchor" scan data under the guide of a constraining fraction overlap parameter and an error tolerance (degree of freedom of fit) parameter. The permutations of possible overlaps are iterated until facial landmarks (such as nose and eyes, or the like) align. The method 200 then proceeds to block 212, where the scan analysis engine 108 conducts fine adjustment to align all scan data of the face in the scan data store 110. In some embodiments, fine adjustment may simply align the first scan data and the second scan data. In some embodiments, additional scans of the face 90 that are stored in the scan data store 110 may also be aligned with each other. In some embodiments, each scan data is realigned until the error tolerance is within 0.001 units. Generally, ten iterations of the fine alignment processing sequence may be used to globally align all scan data, but in some embodiments, more or fewer iterations may be used.

The method 200 then proceeds to a continuation terminal ("terminal A"), and from terminal A (FIG. 2B) to block 214, where the scan analysis engine 108 generates a first eyebag model for the first scan data and a second eyebag model for the second scan data. The eyebag area is a complex surface area that varies from face to face, and so determination of a quantifiably comparable representation of the eyebag area is desired. In some embodiments, the eyebag model is based on a two-dimensional cross-section of the scan data. Such eyebag models are based on vertical cross-sections taken at the middle of each eyebag relative to the corners of each eye, thus allowing for the standardization of a quantifiable analysis of eyebag features. This eyebag model based on a vertical eyebag profile provides useful information on drastic changes, as the loose eyebag skin provides the largest range of deformation distances for measurement. In some embodiments, the eyebag model is based on a three-dimensional representation of the scan data. Such eyebag models may be generated by determining a reference plane within the scan data, and determining a distance from the reference plane for every pixel or voxel of the scan data. One non-limiting example of a reference plane is a midplane or vertical plane located at a midpoint between a furthest forward point of the scan data and a furthest back point of the scan data. The eyebag model in this case may be a histogram of the determined distances from the reference plane.

Figure 3:
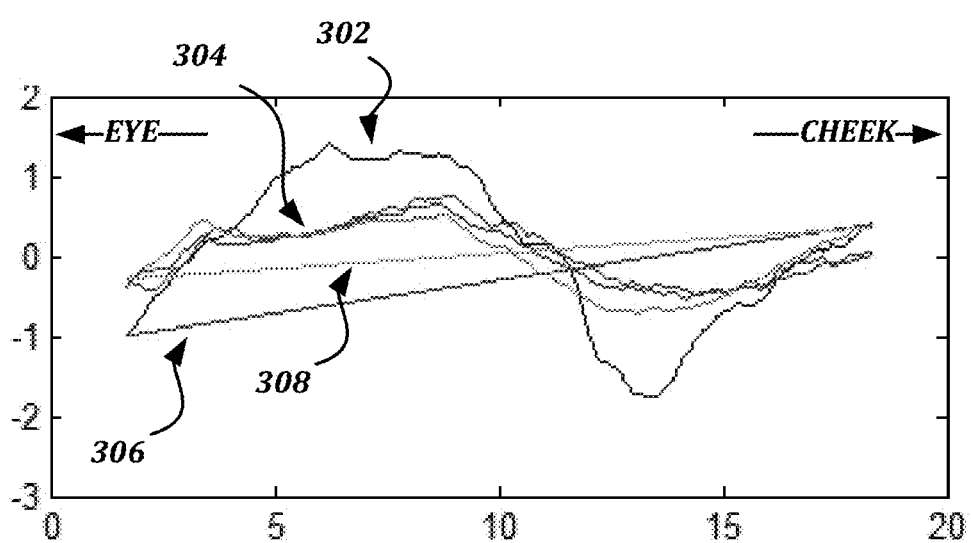
FIG. 3 is a chart that illustrates an example of compared two-dimensional eyebag models according to various aspects of the present disclosure.

FIG. 3 is a chart that illustrates an example of compared two-dimensional eyebag models according to various aspects of the present disclosure. A first eyebag model 302 is illustrated as an "S" shape of a vertical cross section obtained from a first scan of a face before applying a product to the eyebag area. A group of subsequent eyebag models 304 illustrates changes in the vertical cross section over time after the application of a product to the eyebag area. The chart also shows a slope 306 of the eyebag model based on the first scan and a slope 308 of the eyebag models based on the subsequent scans.

Figure 4:
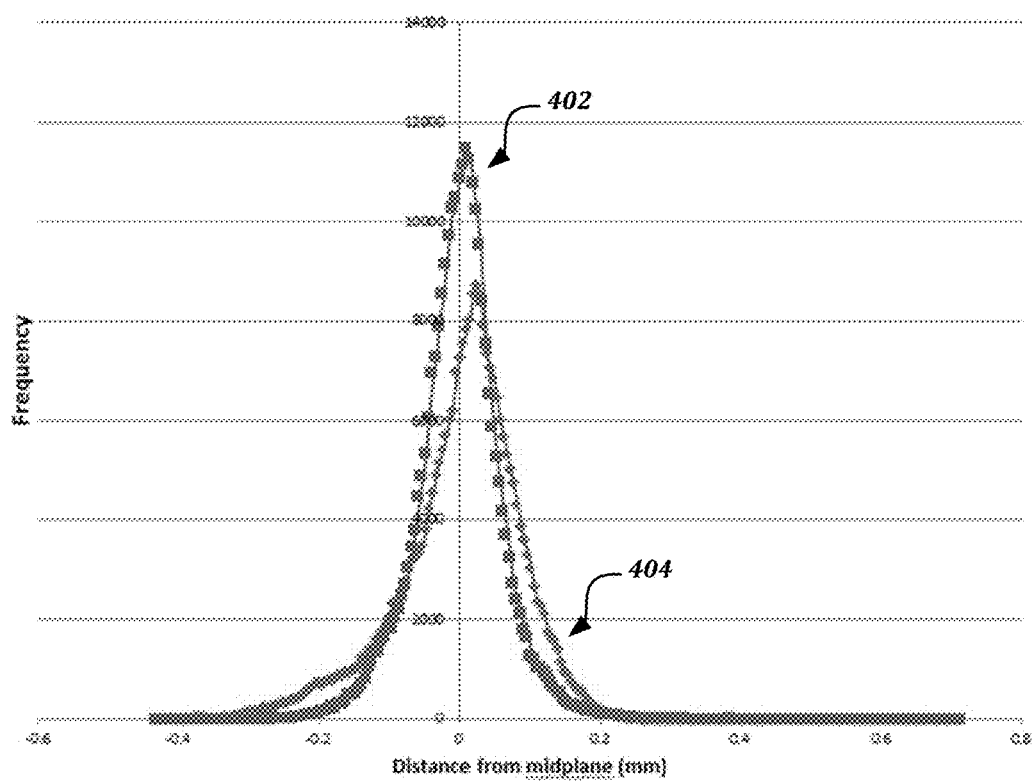
FIG. 4 is a chart that illustrates an example of compared eyebag models based on three-dimensional representations of the scan data.

FIG. 4 is a chart that illustrates an example of compared eyebag models based on three-dimensional representations of the scan data. A first eyebag model 402 is shown as a histogram of distances of pixels or voxels in the scan data to a reference plane of the scan data. A second eyebag model 404 is also shown. To determine a score for such a model, the standard deviation of the histogram may be determined, and the determined standard deviation may be used as the score. Lower scores would indicate improved eyebag appearance, as it would mean that more of the eyebag area is located near the reference plane, and hence the area is smoother or more regularly shaped. In some embodiments, other techniques may be used to determine the score, such as determining a maximum value for the histogram, determining a location on the X axis for the histogram, and/or other suitable techniques.

Returning to FIG. 2B, at block 216 the scan analysis engine 108 generates a difference between the first eyebag model and the second eyebag model. Many suitable forms of quantitative eyebag model measurements may be performed. Some scores or metrics may be calculated for each eyebag model separately and the calculated scores may be compared. In other cases, metrics may be calculated as differences between selected eyebag models. Once the eyebag models are obtained, the scores or metrics may be calculated using any suitable tool, including but not limited to Matlab, custom stand-alone software, and/or the like. In some embodiments, instead of generating a difference between multiple models, a score for a single model may be determined and stored.

Figure 5:
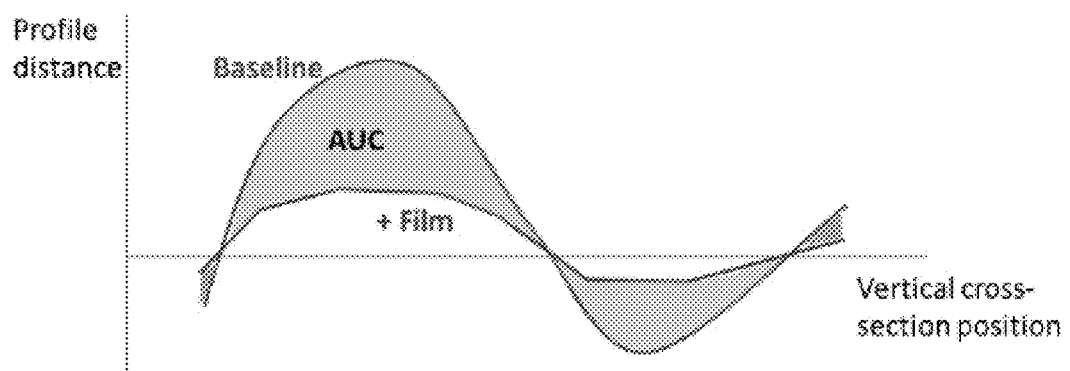
FIG. 5 is a chart that illustrates determination of an absolute area under curve score according to various aspects of the present disclosure.

FIGS. 5-8 illustrate various metrics or scores determined for eyebag profiles based on vertical cross-sections of the eyebag area. FIG. 5 is a chart that illustrates determination of an absolute area under curve score according to various aspects of the present disclosure. For this metric, the area under the curve of the eyebag model relative to the baseline eyebag model indicates an amount of reduction of the eyebag. The larger the area difference, the greater effect of any product that was applied between the baseline face scan and the later face scan.

Figure 6:
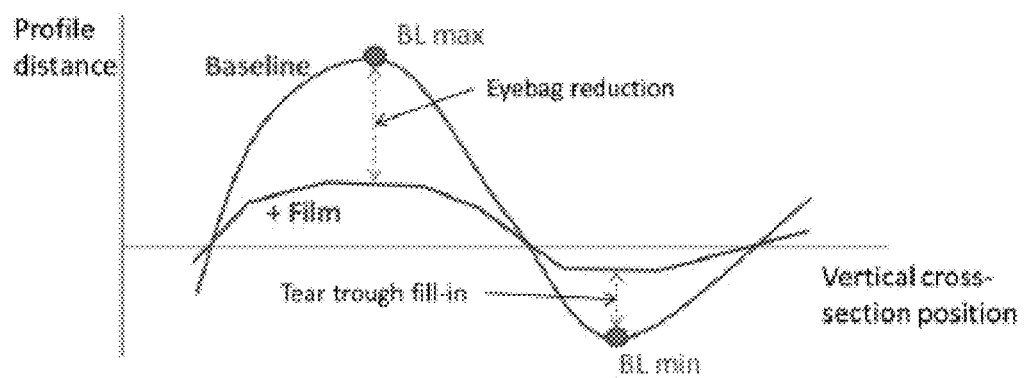
FIG. 6 is a chart that illustrates determination of a maximum/minimum value score according to various aspects of the present disclosure.

FIG. 6 is a chart that illustrates determination of a maximum/minimum value score according to various aspects of the present disclosure. For this metric, the score determined by measuring a height of an eyebag portion of the eyebag model and/or a depth of a tear trough portion of the eyebag model may be calculated, and may be compared between eyebag models to determine the extent of reduction of the eyebag. Larger differences between the maximum values indicate a greater effect of any product that was applied between the baseline face scan and the later face scan. In some embodiments, only the heights of the eyebag portions may be compared. In some embodiments, only the depths of the tear trough portions may be compared. In some embodiments, the differences between the height of the eyebag portions and the depth of the tear trough portions may be combined to produce a combined metric.

Figure 7:
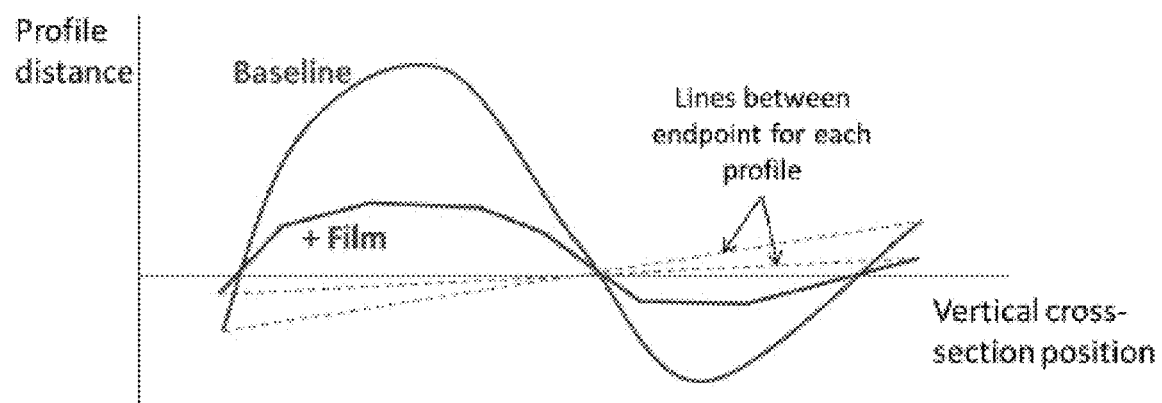
FIG. 7 is a chart that illustrates determination of a slope score according to various aspects of the present disclosure.

FIG. 7 is a chart that illustrates determination of a slope score according to various aspects of the present disclosure. For this metric, a slope from a start point of the eyebag model to the end point of the eyebag model is determined, with a value closer to zero indicating an improvement in the appearance of the eyebag area.

Figure 8:
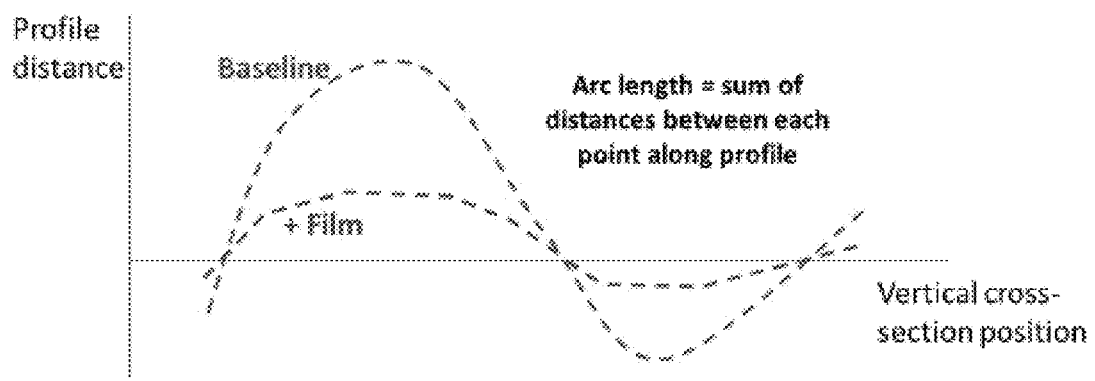
FIG. 8 is a chart that illustrates determination of an arc length score according to various aspects of the present disclosure.

FIG. 8 is a chart that illustrates determination of an arc length score according to various aspects of the present disclosure. Arc length of an eyebag model is related to the slackness of the eyebag and contraction stress produced by a product on the eyebag skin. The larger the internal stress, the smaller the arc length, and therefore greater improvement in the appearance of the eyebag.

Returning to FIG. 2B, the method 200 then proceeds to block 218, where the scan analysis engine 108 stores the difference between the first eyebag model and the second eyebag model in the scan data store. The stored differences have a variety of uses. For example, in some embodiments, the stored differences may be used to quantitatively compare changes in eyebag shape over time, such as before application of a product to the eyebag area and after application of the product to the eyebag area following one or more time periods. Before the present disclosure, such quantitative comparisons were not possible. As another example, in some embodiments, the stored differences may be used to generate predictive models, as described below in optional blocks 220-224. The differences may be stored as absolute differences, as percentages of change, or in any other suitable format. As mentioned above, in some embodiments, a single eyebag model is processed, and the score for the single eyebag model is stored instead of (or in addition to) a difference between models or scores.

At optional block 220, the three-dimensional scanner 102 performs a scan of a new face and provides new scan data to the facial analysis device 104. At optional block 222, the scan analysis engine 108 uses the stored difference between the first eyebag model and the second eyebag model to generate predicted scan data based on the new scan data. For example, the stored difference may indicate a 40% reduction in eyebag height and a 60% reduction in tear trough depth, and so the scan analysis engine 108 would generate predicted scan data in which the eyebag height of the new scan data is reduced by 40% and the tear trough depth of the new scan data is reduced by 60%. In some embodiments, multiple stored differences (instead of just the difference between the first eyebag model and the second eyebag model) could be combined and used to generate the predicted scan data.

Next, at optional block 224, the facial analysis device 104 presents the predicted scan data on a display 106. The predicted scan data would represent what the new face may look like after applying a product that was used between the generation of the first eyebag model and the second eyebag model. Such a presentation can help influence a decision whether or not to use the product, or to help choose between multiple products. Blocks 220-224 are illustrated as optional because some embodiments merely use the difference information just for quantitative comparisons and not for generating predicted scan data. Also, in some embodiments, a single scan may be performed, and a score may be generated based on a single eyebag model as a diagnostic score instead of a comparative difference score. The method 200 then proceeds to an end block and terminates.

Figure 9:
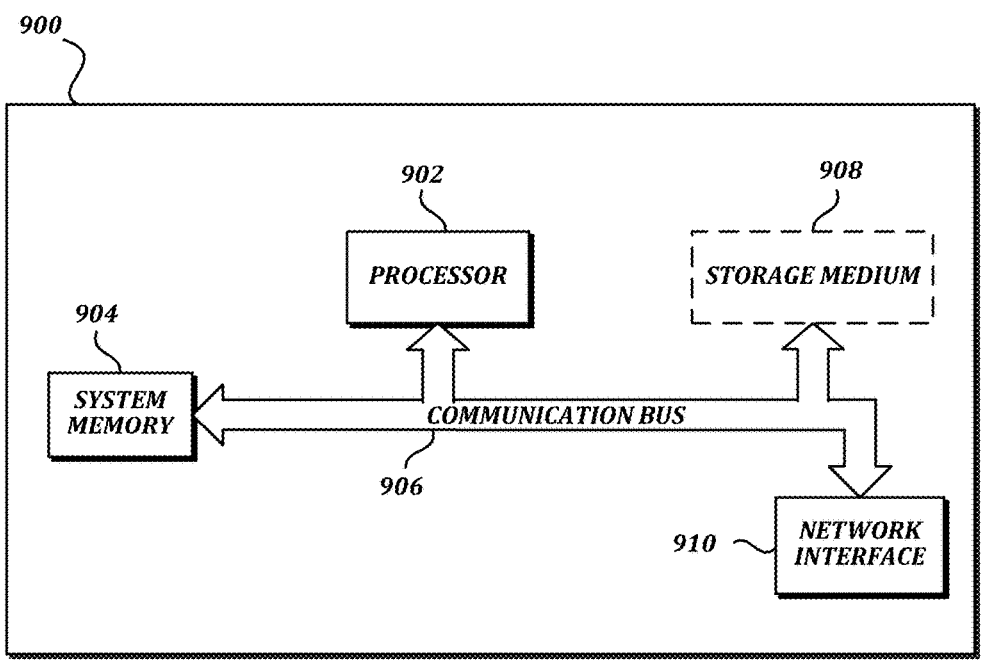
FIG. 9 is a block diagram that illustrates aspects of an exemplary computing device appropriate for use as a computing device of the present disclosure.

FIG. 9 is a block diagram that illustrates aspects of an exemplary computing device 900 appropriate for use as a computing device of the present disclosure. While multiple different types of computing devices were discussed above, the exemplary computing device 900 describes various elements that are common to many different types of computing devices. While FIG. 9 is described with reference to a computing device that is implemented as a device on a network, the description below is applicable to servers, personal computers, mobile phones, smart phones, tablet computers, embedded computing devices, and other devices that may be used to implement portions of embodiments of the present disclosure. Moreover, those of ordinary skill in the art and others will recognize that the computing device 900 may be any one of any number of currently available or yet to be developed devices.

In its most basic configuration, the computing device 900 includes at least one processor 902 and a system memory 904 connected by a communication bus 906. Depending on the exact configuration and type of device, the system memory 904 may be volatile or nonvolatile memory, such as read only memory ("ROM"), random access memory ("RAM"), EEPROM, flash memory, or similar memory technology. Those of ordinary skill in the art and others will recognize that system memory 904 typically stores data and/or program modules that are immediately accessible to and/or currently being operated on by the processor 902. In this regard, the processor 902 may serve as a computational center of the computing device 900 by supporting the execution of instructions.

As further illustrated in FIG. 9, the computing device 900 may include a network interface 910 comprising one or more components for communicating with other devices over a network. Embodiments of the present disclosure may access basic services that utilize the network interface 910 to perform communications using common network protocols. The network interface 910 may also include a wireless network interface configured to communicate via one or more wireless communication protocols, such as WiFi, 2G, 3G, LTE, WiMAX, Bluetooth, Bluetooth low energy, and/or the like. As will be appreciated by one of ordinary skill in the art, the network interface 910 illustrated in FIG. 9 may represent one or more wireless interfaces or physical communication interfaces described and illustrated above with respect to particular components of the system 100.

In the exemplary embodiment depicted in FIG. 9, the computing device 900 also includes a storage medium 908. However, services may be accessed using a computing device that does not include means for persisting data to a local storage medium. Therefore, the storage medium 908 depicted in FIG. 9 is represented with a dashed line to indicate that the storage medium 908 is optional. In any event, the storage medium 908 may be volatile or nonvolatile, removable or nonremovable, implemented using any technology capable of storing information such as, but not limited to, a hard drive, solid state drive, CD ROM, DVD, or other disk storage, magnetic cassettes, magnetic tape, magnetic disk storage, and/or the like.

As used herein, the term "computer-readable medium" includes volatile and non-volatile and removable and non-removable media implemented in any method or technology capable of storing information, such as computer readable instructions, data structures, program modules, or other data. In this regard, the system memory 904 and storage medium 908 depicted in FIG. 9 are merely examples of computer-readable media.

Suitable implementations of computing devices that include a processor 902, system memory 904, communication bus 906, storage medium 908, and network interface 910 are known and commercially available. For ease of illustration and because it is not important for an understanding of the claimed subject matter, FIG. 9 does not show some of the typical components of many computing devices. In this regard, the computing device 900 may include input devices, such as a keyboard, keypad, mouse, microphone, touch input device, touch screen, tablet, and/or the like. Such input devices may be coupled to the computing device 900 by wired or wireless connections including RF, infrared, serial, parallel, Bluetooth, Bluetooth low energy, USB, or other suitable connections protocols using wireless or physical connections. Similarly, the computing device 900 may also include output devices such as a display, speakers, printer, etc. Since these devices are well known in the art, they are not illustrated or described further herein.

Certain embodiments disclosed herein utilize circuitry in order to implement functionality, operably couple to or more components, generate information, determine operation conditions, and the like. Circuitry of any type can be used. In some embodiments, circuitry includes, among other things, one or more computing devices such as a processor (e.g., a microprocessor), a central processing unit (CPU), a digital signal processor (DSP), an application-specific integrated circuit (ASIC), a field-programmable gate array (FPGA), or the like, or any combinations thereof, and can include discrete digital or analog circuit elements or electronics, or combinations thereof. In some embodiments, circuitry includes one or more ASICs having a plurality of predefined logic components. In some embodiments, circuitry includes one or more FPGA having a plurality of programmable logic components.

While illustrative embodiments have been illustrated and described, it will be appreciated that various changes can be made therein without departing from the spirit and scope of the invention.

The embodiments of the invention in which an exclusive property or privilege is claimed are defined as follows:

1. A computer-implemented method of processing three-dimensional face scan data, the method comprising:
    applying a treatment to an eyebag area of a face;
    receiving, by a facial analysis device, first face scan data representing a three-dimensional scan of the face;
    determining, by the facial analysis device, a first model of an eyebag area of the first face scan data;
    determining, by the facial analysis device, a first score based on the first model;
    storing by the facial analysis device, the first score in a scan data store;
    comparing, by the facial analysis device, the first model to at least one stored model of previous face scan data representing a previous three-dimensional scan of the face to determine differences between the models;
    presenting, by the facial analysis device, the determined differences in order to evaluate the treatment; and
    storing, by the facial analysis device, the determined differences in the scan data store.

2. The method of claim 1, further comprising:
    receiving, by the facial analysis device, new face scan data representing a three-dimensional scan of a new face;
    determining, by the facial analysis device, a new model of an eyebag area of the new face scan data;
    determining, by the facial analysis device, predicted face scan data using the new model and the determined differences stored in the scan data store; and
    presenting, by the facial analysis device, the predicted face scan data on a display.

3. The method of claim 1, wherein determining the first model of the eyebag area of the first face scan data includes determining a vertical cross-section of the eyebag area at a middle of the eyebag area relative to corners of an associated eye.

4. The method of claim 3, wherein determining the first score based on the first model includes at least one of:
    determining an absolute area under curve (AUC) for the first model;
    determining a max value or min value for the first model;
    determining a slope between curve endpoints for the first model; and
    determining an arc length for the first model.

5. The method of claim 1, wherein determining the first model of the eyebag area of the first face scan data includes:
    determining a reference plane of the first face scan data;
    determining a distance from each voxel within the first face scan data to the reference plane; and
    determining a histogram of the distances; and
    wherein determining a first score based on the first model includes determining a standard deviation of the histogram.

6. The method of claim 1, further comprising aligning the first face scan data to previous face scan data by:
    performing pair-wise coarse adjustment to align the first face scan data with second face scan data; and
    performing global fine adjustment to iteratively realign all face scan data until an error tolerance is within a predetermined threshold.

7. The method of claim 6, wherein performing pair-wise coarse adjustment to align the first face scan data with the second face scan data includes iteratively aligning the first face scan data to the second face scan data under the guide of a constraining fraction overlap parameter and an error tolerance parameter until facial landmarks align.

8. A system for processing three-dimensional face scan data, the system comprising:
    a three-dimensional scanner; and
    a facial analysis device communicatively coupled to the scanner and configured to perform actions including:
        receiving, from the three-dimensional scanner, first face scan data representing a three-dimensional scan of a face after application of a treatment to an eyebag area of the face;
        determining a first model of an eyebag area of the first face scan data;
        determining a first score based on the first model;
        storing the first score in a scan data store;
        comparing the first model to at least one stored model of previous face scan data representing a previous three-dimensional scan of the face from before application of the treatment to determine differences between the models;
        presenting the determined differences in order to evaluate the treatment; and
        storing the determined differences in the scan data store.

9. The system of claim 8, further comprising a display, and wherein the actions further include:
    receiving, from the scanner, new face scan data representing a three-dimensional scan of a new face;
    determining a new model of an eyebag area of the new face scan data;
    determining predicted face scan data using the new model and the determined differences stored in the scan data store; and
    presenting, on the display, the predicted face scan data.

10. The system of claim 8, wherein determining the first model of the eyebag area of the first face scan data includes determining a vertical cross-section of the eyebag area at a middle of the eyebag area relative to corners of an associated eye.

11. The system of claim 10, wherein determining the first score based on the first model includes at least one of:
  determining an absolute area under curve (AUC) for the first model;
  determining a maximum value or minimum value for the first model;
  determining a slope between curve endpoints for the first model; and
  determining an arc length for the first model.

12. The system of claim 8, wherein determining the first model of the eyebag area of the first face scan data includes:
  determining a reference plane of the first face scan data;
  determining a distance from each voxel within the first face scan data to the reference plane; and
  determining a histogram of the distances; and
  wherein determining the first score based on the first model includes determining a standard deviation of the histogram.

13. The system of claim 8, wherein the actions further include aligning the first face scan data to previous face scan data by:
  performing pair-wise coarse adjustment to align the first face scan data with second face scan data; and
  performing global fine adjustment to iteratively realign all face scan data until an error tolerance is within a predetermined threshold.

14. The system of claim 13, wherein performing pair-wise coarse adjustment to align the first face scan data with the second face scan data includes iteratively aligning the first face scan data to the second face scan data under the guide of a constraining fraction overlap parameter and an error tolerance parameter until facial landmarks align.

15. A system for processing three-dimensional face scan data, the system comprising:
  circuitry for receiving first face scan data representing a three-dimensional scan of a face after application of a treatment to an eyebag area of the face;
  circuitry for determining a first model of an eyebag area of the first face scan data;
  circuitry for determining a first score based on the first model;
  circuitry for storing the first score in a scan data store;
  circuitry for comparing the first model to at least one stored model of previous face scan data representing a previous three-dimensional scan of the face from before application of the treatment to determine differences between the models;
  circuitry for presenting the determined differences in order to evaluate the treatment; and
  circuitry for storing the determined differences in the scan data store.

16. The system of claim 15, wherein the first model is a vertical cross-section of the eyebag area at the middle of the eyebag area relative to corners of an associated eye, and wherein determining the first score based on the first model includes at least one of:
  determining a difference in absolute area under curve (AUC) for the first model and the at least one stored model;
  determining a difference in max value or min value for the first model and the at least one stored model;
  determining a difference in slope between curve endpoints for the first model and the at least one stored model; and
  determining a difference in arc length for the first model and the at least one stored model.

* * * * *